United States Patent [19]

Hoff

[11] Patent Number: Plant 7,026

[45] Date of Patent: Sep. 12, 1989

[54] LILY PLANT NAMED CHICAGO

[75] Inventor: Petrus M. M. Hoff, Hem, Netherlands

[73] Assignee: De besloten vennootschap met beperkte aansprakelijkheid Hoffgaarde B.V., Netherlands

[21] Appl. No.: 254,200

[22] Filed: Oct. 6, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A lily plant named Chicago having strong stems, bright yellow flowers, floriferous habit, medium green foliage, excellent keeping quality when cut, and relatively fast growth to flowering.

3 Drawing Sheets

1

The present invention comprises a new and distinct cultivar of lily, botanically known as Lilium, and hereinafter referred to by the cultivar name Chicago.

Chicago is a product of a planned breeding program which had the objective of creating new lily cultivars with strong and long stems, high flower production from relatively small bulbs, bright colors, superior quality and strength when cut, and relatively short growth time in the greenhouse. These traits in combination were not available or needed improvement in existing cultivars.

Chicago was originated from a hybridization made by the inventor in a controlled breeding program in Hoffgaarde B.V. Hemmerbuurt 205, Hem, Holland in 1980. The male and female parents were seedlings which are not known at this time.

Chicago was discovered and selected as one flowering plant within the progeny of the stated cross by the inventor in June 1982 in a controlled environment in Hem, the Netherlands.

The first act of asexual reproduction of Chicago was accomplished by scaling of the bulbs of the initial selection in September 1982 by the inventor in a controlled environment in Hem, the Netherlands. Horticultural examination of selected units initiated in July 1983 has demonstrated that the combination of characteristics as herein disclosed for Chicago are firmly fixed and are retained through successive generations of asexual reproduction.

Chicago has not been observed under all possible environmental conditions. The phenotype may vary significantly with variations in environment such as temperature, light intensity, and day length. The following observations, measurements, and comparisons describe plants grown in Hem, the Netherlands under greenhouse conditions which approximate those generally used in commercial practice.

The following traits have been repeatedly observed and are determined to be basic characteristics of Chicago which in combination distinguish this lily as a new and distinct cultivar.

1. The height of a fully grown plant is approximately 160 cm.
2. The diameter of the flowers is approximately 16 cm.
3. The flower color is a bright yellow.
4. The leaves are medium green in color.
5. Size 10–12 produces an average of 4–8 flowers.

2

Of the many commercial cultivars known to the present inventor, the most similar in comparison to Chicago in Yellow Blaze. In comparison to Chicago, Yellow Blaze has weaker stems, fewer flowers on the same bulb size, longer growing time to flowering, and weaker flowers.

The accompanying photographic drawings show the characteristics of Chicago, with colors being as true as possible with illustrations of this type. The first photograph illustrates foliage near the base of a specimen plant. The second photograph shows the prolific budding habit of Chicago, and the third photograph illustrates several flowers in bloom.

In the following description, color references are made to The Royal Horticultural Society Colour Chart. The color values were determined at approximately 8 a.m. on June 8, 1988 under cloudy conditions at Hem, the Netherlands.

THE PLANT

Parentage:
- *Seed parent.*—Seedling (unknown).
- *Pollen parent.*—Seedling (unknown).

Classification:
- *Botanic.*—Lilium.
- *Commercial.*—Lily, cv Chicago.

Form: Asiatic hybrid.
Height: 160 cm.
Growth habit: Vigorous.
Strength: Very strong stems.
Foliage:
- *Quantity.*—Medium.
- *Size of leaf.*—Approximately 9 cm. long and 2 cm. wide.
- *Shape of leaf.*—Ovate.
- *Texture.*—Strong, thick.
- *Color.*—147A.

Bulbs:
- *Size.*—Maximum, approximately 20 cm.
- *Color.*—White.

THE BUD

Form: Ovate.
Size: Average.
Color: Light green to yellow 12A just before opening.
Tepals: 6.
Peduncle: Umbellate.

THE FLOWER

Blooming habit: Erect, deep corolla, very floriferous.
Size: Medium.
Borne: On strong peduncles.
Shape: Relatively flat.
Tepalage:
*Number of tepals.*—6.
*Arrangement.*—Normal.
*Color.*—Upper surface: 12A. Lower surface: 12A.
*Tepal longevity.*—Excellent.
*Spotting.*—Medium.
Pedicel:
*Length.*—Average.
*Color.*—Green.
*Form.*—Erect.
Appearance: Relatively shiny.

Disease resistance: Excellent.
Lasting quality: Excellent.

REPRODUCTIVE ORGANS

Stamens, anthers:
*Arrangement.*—Normal.
*Length.*—Normal.
*Number.*—6.
Pistels: Medium.

FRUIT

Fertility: Normal.

I claim:

1. A new and distinct cultivar of lily plant named Chicago, as illustrated and described.

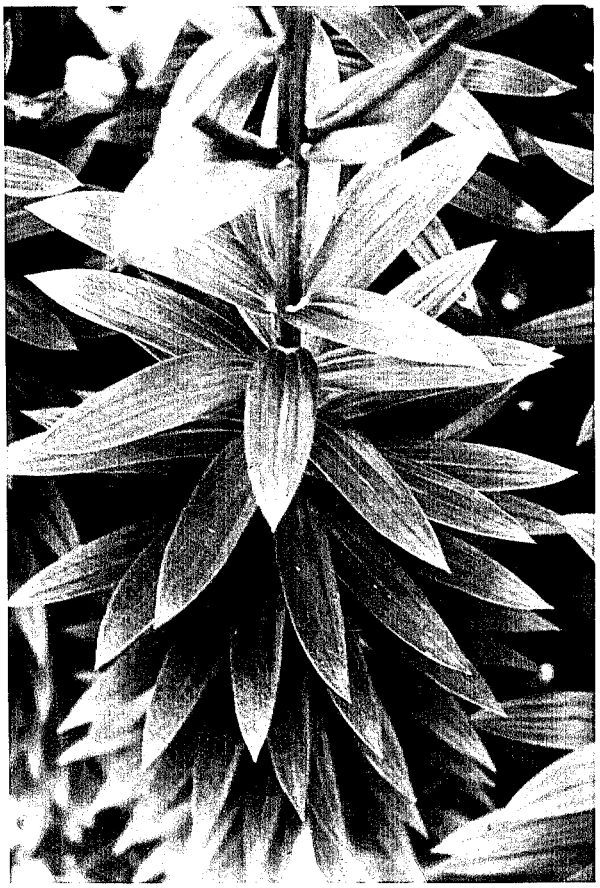

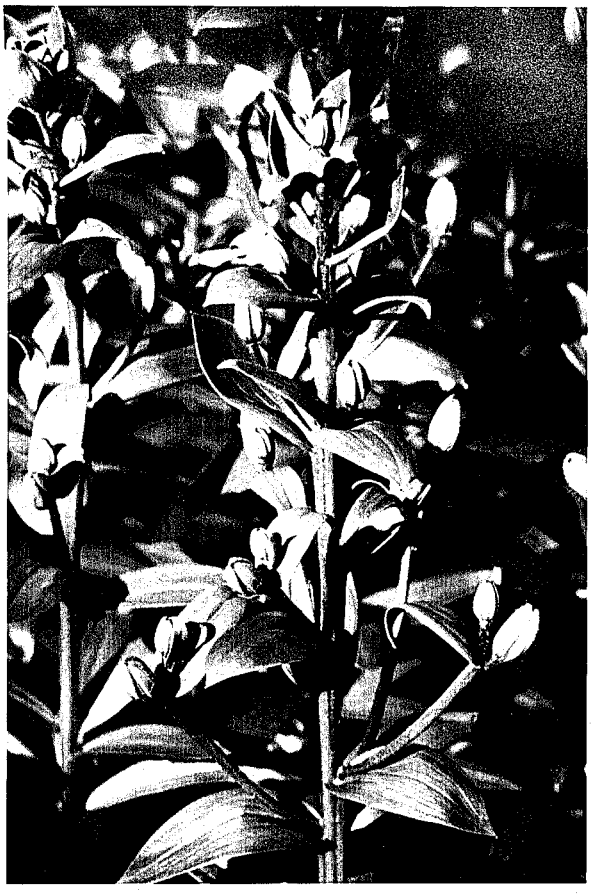

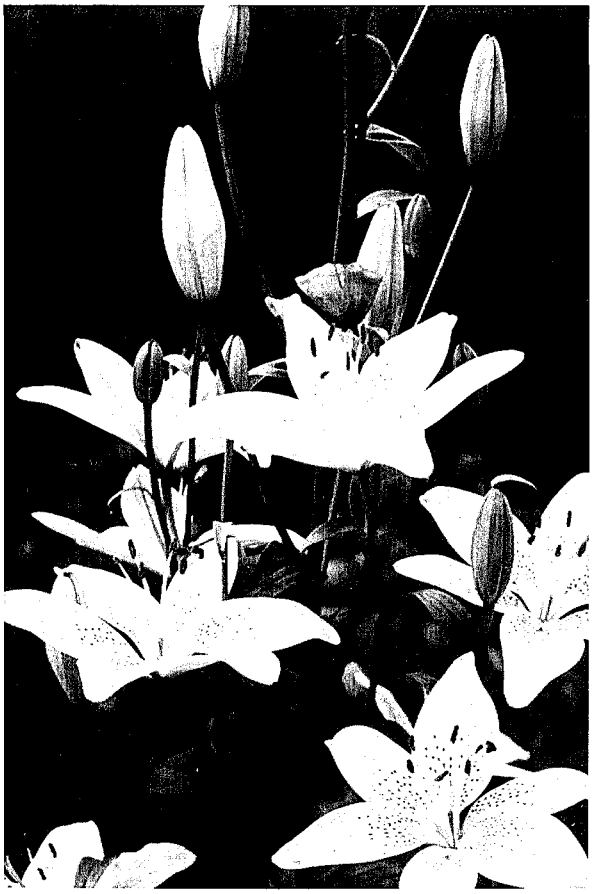

* * * * *